(12) United States Patent
Kollar et al.

(10) Patent No.: US 11,653,916 B2
(45) Date of Patent: May 23, 2023

(54) SURGICAL BUTTRESS FOR CIRCULAR STAPLING

(71) Applicant: Covidien LP, Mansfield, MA (US)

(72) Inventors: Charles R. Kollar, Washington, DC (US); Kevin R. Fogarty, NY, NY (US)

(73) Assignee: Covidien LP, Mansfield, MA (US)

(*) Notice: Subject to any disclaimer, the term of this patent is extended or adjusted under 35 U.S.C. 154(b) by 0 days.

(21) Appl. No.: 17/499,180

(22) Filed: Oct. 12, 2021

(65) Prior Publication Data

US 2022/0022879 A1 Jan. 27, 2022

Related U.S. Application Data

(63) Continuation of application No. 16/189,601, filed on Nov. 13, 2018, now Pat. No. 11,141,151.

(Continued)

(51) Int. Cl.
*A61B 17/064* (2006.01)
*A61B 17/072* (2006.01)
*A61B 17/115* (2006.01)

(52) U.S. Cl.
CPC ...... *A61B 17/072* (2013.01); *A61B 17/07292* (2013.01); *A61B 17/1155* (2013.01);
(Continued)

(58) Field of Classification Search
CPC .... A61B 17/07292; A61B 2017/00004; A61B 2017/0404
See application file for complete search history.

(56) References Cited

U.S. PATENT DOCUMENTS 3,054,406 A 9/1962 Usher
3,079,606 A 3/1963 Bobrov et al.
(Continued)

FOREIGN PATENT DOCUMENTS

CA 2282761 A1 9/1998
DE 1602563 U 3/1950
(Continued)

OTHER PUBLICATIONS

Australian Examination Report No. 1 corresponding to AU 2014200793 dated Sep. 2, 2017.
(Continued)

*Primary Examiner* — Eyamindae C Jallow
(74) *Attorney, Agent, or Firm* — Carter, DeLuca & Farrell LLP

(57) ABSTRACT

A surgical stapling apparatus includes a staple cartridge assembly, an anvil assembly operatively associated with the staple cartridge assembly, and a surgical buttress. The staple cartridge assembly includes a tissue facing surface having staple retaining slots defined therein, each staple retaining slot housing a staple therein, and an annular knife disposed radially inwardly of the tissue facing surface. The anvil assembly includes an anvil member including a tissue facing surface having staple forming recesses defined therein, and an anvil shaft extending from the anvil member. The surgical buttress is releasably disposed on the tissue facing surface of the staple cartridge assembly or the anvil assembly. The surgical buttress has an annular configuration defining a central aperture therethrough, and includes body segments extending radially outwardly about the central aperture in spaced radial relation relative to each other, and a ring segment interconnecting the body segments.

20 Claims, 3 Drawing Sheets

Related U.S. Application Data

(60) Provisional application No. 62/596,146, filed on Dec. 8, 2017.

(52) U.S. Cl.
CPC .............. *A61B 2017/07257* (2013.01); *A61B 2017/07271* (2013.01)

(56) References Cited

U.S. PATENT DOCUMENTS

| | | | |
|---|---|---|---|
| 3,124,136 A | 3/1964 | Usher | |
| 3,364,200 A | 1/1968 | Ashton et al. | |
| 3,499,591 A | 3/1970 | Green | |
| 3,797,494 A | 3/1974 | Zaffaroni | |
| 3,939,068 A | 2/1976 | Wendt et al. | |
| 3,948,666 A | 4/1976 | Kitanishi et al. | |
| 4,064,062 A | 12/1977 | Yurko | |
| 4,166,800 A | 9/1979 | Fong | |
| 4,282,236 A | 8/1981 | Broom | |
| 4,347,847 A | 9/1982 | Usher | |
| 4,354,628 A | 10/1982 | Green | |
| 4,416,698 A | 11/1983 | McCorsley, III | |
| 4,429,695 A | 2/1984 | Green | |
| 4,452,245 A | 6/1984 | Usher | |
| 4,473,077 A | 9/1984 | Noiles et al. | |
| 4,576,167 A | 3/1986 | Noiles | |
| 4,605,730 A | 8/1986 | Shalaby et al. | |
| 4,626,253 A | 12/1986 | Broadnax, Jr. | |
| 4,655,221 A | 4/1987 | Devereux | |
| 4,834,090 A | 5/1989 | Moore | |
| 4,838,884 A | 6/1989 | Dumican et al. | |
| 4,927,640 A | 5/1990 | Dahlinder et al. | |
| 4,930,674 A | 6/1990 | Barak | |
| 5,002,551 A | 3/1991 | Linsky et al. | |
| 5,005,749 A | 4/1991 | Aranyi | |
| 5,014,899 A | 5/1991 | Presty et al. | |
| 5,040,715 A | 8/1991 | Green et al. | |
| 5,057,334 A | 10/1991 | Vail | |
| 5,065,929 A | 11/1991 | Schulze et al. | |
| 5,112,496 A | 5/1992 | Dhawan et al. | |
| 5,119,983 A | 6/1992 | Green et al. | |
| 5,162,430 A | 11/1992 | Rhee et al. | |
| 5,205,459 A | 4/1993 | Brinkerhoff et al. | |
| 5,263,629 A | 11/1993 | Trumbull et al. | |
| 5,281,197 A | 1/1994 | Arias et al. | |
| 5,307,976 A | 5/1994 | Olson et al. | |
| 5,312,023 A | 5/1994 | Green et al. | |
| 5,314,471 A | 5/1994 | Brauker et al. | |
| 5,318,221 A | 6/1994 | Green et al. | |
| 5,324,775 A | 6/1994 | Rhee et al. | |
| 5,326,013 A | 7/1994 | Green et al. | |
| 5,332,142 A | 7/1994 | Robinson et al. | |
| 5,344,454 A | 9/1994 | Clarke et al. | |
| 5,392,979 A | 2/1995 | Green et al. | |
| 5,397,324 A | 3/1995 | Carroll et al. | |
| 5,405,072 A | 4/1995 | Zlock et al. | |
| 5,410,016 A | 4/1995 | Hubbell et al. | |
| 5,425,745 A | 6/1995 | Green et al. | |
| 5,441,193 A | 8/1995 | Gravener | |
| 5,441,507 A | 8/1995 | Wilk | |
| 5,443,198 A | 8/1995 | Viola et al. | |
| 5,468,253 A | 11/1995 | Bezwada et al. | |
| 5,484,913 A | 1/1996 | Stilwell et al. | |
| 5,503,638 A | 4/1996 | Cooper et al. | |
| 5,514,379 A | 5/1996 | Weissleder et al. | |
| 5,542,594 A | 8/1996 | McKean et al. | |
| 5,543,441 A | 8/1996 | Rhee et al. | |
| 5,549,628 A | 8/1996 | Cooper et al. | |
| 5,550,187 A | 8/1996 | Rhee et al. | |
| 5,575,803 A | 11/1996 | Cooper et al. | |
| 5,588,579 A | 12/1996 | Schnut et al. | |
| 5,645,915 A | 7/1997 | Kranzler et al. | |
| 5,653,756 A | 8/1997 | Clarke et al. | |
| 5,683,809 A | 11/1997 | Freeman et al. | |
| 5,690,675 A | 11/1997 | Sawyer et al. | |
| 5,702,409 A | 12/1997 | Rayburn et al. | |
| 5,752,965 A | 5/1998 | Francis et al. | |
| 5,752,974 A | 5/1998 | Rhee et al. | |
| 5,762,256 A | 6/1998 | Mastri et al. | |
| 5,766,188 A | 6/1998 | Igaki | |
| 5,769,892 A | 6/1998 | Kingwell | |
| 5,782,396 A | 7/1998 | Mastri et al. | |
| 5,799,857 A | 9/1998 | Robertson et al. | |
| 5,810,855 A | 9/1998 | Rayburn et al. | |
| 5,814,057 A | 9/1998 | Oi et al. | |
| 5,819,350 A | 10/1998 | Wang | |
| 5,833,695 A | 11/1998 | Yoon | |
| 5,843,096 A | 12/1998 | Igaki et al. | |
| 5,871,135 A | 2/1999 | Williamson, IV et al. | |
| 5,874,500 A | 2/1999 | Rhee et al. | |
| 5,895,412 A | 4/1999 | Tucker | |
| 5,895,415 A | 4/1999 | Chow et al. | |
| 5,902,312 A | 5/1999 | Frater et al. | |
| 5,908,427 A | 6/1999 | McKean et al. | |
| 5,915,616 A | 6/1999 | Viola et al. | |
| 5,931,847 A | 8/1999 | Bittner et al. | |
| 5,957,363 A | 9/1999 | Heck | |
| 5,964,774 A | 10/1999 | McKean et al. | |
| 5,997,895 A | 12/1999 | Narotam et al. | |
| 6,019,791 A | 2/2000 | Wood | |
| 6,030,392 A | 2/2000 | Dakov | |
| 6,032,849 A | 3/2000 | Mastri et al. | |
| 6,045,560 A | 4/2000 | McKean et al. | |
| 6,053,390 A | 4/2000 | Green et al. | |
| 6,063,097 A | 5/2000 | Oi et al. | |
| 6,080,169 A | 6/2000 | Turtel | |
| 6,093,557 A | 7/2000 | Pui et al. | |
| 6,099,551 A | 8/2000 | Gabbay | |
| 6,142,933 A | 11/2000 | Longo et al. | |
| 6,149,667 A | 11/2000 | Hovland et al. | |
| 6,152,943 A | 11/2000 | Sawhney | |
| 6,155,265 A | 12/2000 | Hammerslag | |
| 6,156,677 A | 12/2000 | Brown Reed et al. | |
| 6,165,201 A | 12/2000 | Sawhney et al. | |
| 6,179,862 B1 | 1/2001 | Sawhney | |
| 6,210,439 B1 | 4/2001 | Firmin et al. | |
| 6,214,020 B1 | 4/2001 | Mulhauser et al. | |
| 6,241,139 B1 | 6/2001 | Milliman et al. | |
| 6,258,107 B1 | 7/2001 | Balazs et al. | |
| 6,267,772 B1 | 7/2001 | Mulhauser et al. | |
| 6,270,530 B1 | 8/2001 | Eldridge et al. | |
| 6,273,897 B1 | 8/2001 | Dalessandro et al. | |
| 6,280,453 B1 | 8/2001 | Kugel et al. | |
| 6,299,631 B1 | 10/2001 | Shalaby | |
| 6,309,569 B1 | 10/2001 | Farrar et al. | |
| 6,312,457 B1 | 11/2001 | DiMatteo et al. | |
| 6,312,474 B1 | 11/2001 | Francis et al. | |
| 6,325,810 B1 | 12/2001 | Hamilton et al. | |
| 6,330,965 B1 | 12/2001 | Milliman et al. | |
| 6,399,362 B1 | 6/2002 | Pui et al. | |
| 6,436,030 B2 | 8/2002 | Rehil | |
| 6,454,780 B1 | 9/2002 | Wallace | |
| 6,461,368 B2 | 10/2002 | Fogarty et al. | |
| 6,500,777 B1 | 12/2002 | Wiseman et al. | |
| 6,503,257 B2 * | 1/2003 | Grant ............... | A61B 17/07207 606/232 |
| 6,514,283 B2 | 2/2003 | DiMatteo et al. | |
| 6,514,534 B1 | 2/2003 | Sawhney | |
| 6,517,566 B1 | 2/2003 | Hovland et al. | |
| 6,551,356 B2 | 4/2003 | Rousseau | |
| 6,566,406 B1 | 5/2003 | Pathak et al. | |
| 6,568,398 B2 | 5/2003 | Cohen | |
| 6,590,095 B1 | 7/2003 | Schleicher et al. | |
| 6,592,597 B2 | 7/2003 | Grant et al. | |
| 6,605,294 B2 | 8/2003 | Sawhney | |
| 6,610,006 B1 | 8/2003 | Amid et al. | |
| 6,627,749 B1 | 9/2003 | Kumar | |
| 6,638,285 B2 | 10/2003 | Gabbay | |
| 6,652,594 B2 | 11/2003 | Francis et al. | |
| 6,656,193 B2 | 12/2003 | Grant et al. | |
| 6,656,200 B2 | 12/2003 | Li et al. | |
| 6,669,735 B1 | 12/2003 | Pelissier | |
| 6,673,093 B1 | 1/2004 | Sawhney | |
| 6,677,258 B2 | 1/2004 | Carroll et al. | |

(56) References Cited

U.S. PATENT DOCUMENTS

| | | |
|---|---|---|
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,843,252 B2 | 1/2005 | Harrison et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,953,139 B2 | 10/2005 | Milliman et al. |
| 6,959,851 B2 | 11/2005 | Heinrich |
| 7,009,034 B2 | 3/2006 | Pathak et al. |
| 7,025,772 B2 | 4/2006 | Gellman et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |
| 7,210,810 B1 | 5/2007 | Iversen et al. |
| 7,214,727 B2 | 5/2007 | Kwon et al. |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,308,998 B2 | 12/2007 | Mastri et al. |
| 7,311,720 B2 | 12/2007 | Mueller et al. |
| 7,328,829 B2 | 2/2008 | Arad et al. |
| 7,334,717 B2 | 2/2008 | Rethy et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,464,849 B2 | 12/2008 | Shelton, IV et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,592,418 B2 | 9/2009 | Pathak et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,635,073 B2 | 12/2009 | Heinrich |
| 7,645,874 B2 | 1/2010 | Saferstein et al. |
| 7,649,089 B2 | 1/2010 | Kumar et al. |
| 7,655,288 B2 | 2/2010 | Bauman et al. |
| 7,662,409 B2 | 2/2010 | Masters |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,673,782 B2 | 3/2010 | Hess et al. |
| 7,708,180 B2 | 5/2010 | Murray et al. |
| 7,709,631 B2 | 5/2010 | Harris et al. |
| 7,717,313 B2 | 5/2010 | Criscuolo et al. |
| 7,722,642 B2 | 5/2010 | Williamson, IV et al. |
| 7,735,703 B2 | 6/2010 | Morgan et al. |
| 7,744,627 B2 | 6/2010 | Orban, III et al. |
| 7,754,002 B2 | 7/2010 | Maase et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,819,896 B2 | 10/2010 | Racenet |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,025,199 B2 | 9/2011 | Whitman et al. |
| 8,028,883 B2 | 10/2011 | Stopek |
| 8,033,483 B2 | 10/2011 | Fortier et al. |
| 8,033,983 B2 | 10/2011 | Chu et al. |
| 8,038,045 B2 | 10/2011 | Bettuchi et al. |
| 8,062,330 B2 | 11/2011 | Prommersberger et al. |
| 8,062,673 B2 | 11/2011 | Figuly et al. |
| 8,083,119 B2 | 12/2011 | Prommersberger |
| 8,091,756 B2 | 1/2012 | Viola |
| 8,123,766 B2 | 2/2012 | Bauman et al. |
| 8,123,767 B2 | 2/2012 | Bauman et al. |
| 8,127,975 B2 | 3/2012 | Olson et al. |
| 8,133,336 B2 | 3/2012 | Kettlewell et al. |
| 8,133,559 B2 | 3/2012 | Lee et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,177,797 B2 | 5/2012 | Shimoji et al. |
| 8,178,746 B2 | 5/2012 | Hildeberg et al. |
| 8,192,460 B2 | 6/2012 | Orban, III et al. |
| 8,201,720 B2 | 6/2012 | Hessler |
| 8,210,414 B2 | 7/2012 | Bettuchi et al. |
| 8,210,453 B2 | 7/2012 | Hull et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,252,339 B2 | 8/2012 | Figuly et al. |
| 8,252,921 B2 | 8/2012 | Vignon et al. |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,317,790 B2 | 11/2012 | Bell et al. |
| 8,322,590 B2 | 12/2012 | Patel et al. |
| 8,348,126 B2 | 1/2013 | Olson et al. |
| 8,348,130 B2 | 1/2013 | Shah et al. |
| 8,365,972 B2 | 2/2013 | Aranyi et al. |
| 8,367,089 B2 | 2/2013 | Wan et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,408,480 B2 | 4/2013 | Hull et al. |
| 8,413,869 B2 | 4/2013 | Heinrich |

(56) References Cited

U.S. PATENT DOCUMENTS

| | | |
|---|---|---|
| 8,413,871 B2 | 4/2013 | Racenet et al. |
| 8,418,909 B2 | 4/2013 | Kostrzewski |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,470,360 B2 | 6/2013 | McKay |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,518,440 B2 | 8/2013 | Blaskovich et al. |
| 8,529,600 B2 | 9/2013 | Woodard, Jr. et al. |
| 8,540,128 B2 | 9/2013 | Shelton, IV et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,579,990 B2 | 11/2013 | Priewe |
| 8,584,920 B2 | 11/2013 | Hodgkinson |
| 8,590,762 B2 | 11/2013 | Hess et al. |
| 8,616,430 B2 | 12/2013 | Stopek et al. |
| 8,617,132 B2 | 12/2013 | Golzarian et al. |
| 8,631,989 B2 | 1/2014 | Aranyi et al. |
| 8,668,129 B2 | 3/2014 | Olson |
| 8,678,263 B2 | 3/2014 | Viola |
| 8,679,137 B2 | 3/2014 | Bauman et al. |
| 8,684,250 B2 | 4/2014 | Bettuchi et al. |
| 8,701,958 B2 | 4/2014 | Shelton, IV et al. |
| 8,721,703 B2 | 5/2014 | Fowler |
| 8,727,197 B2 | 5/2014 | Hess et al. |
| 8,757,466 B2 | 6/2014 | Olson et al. |
| 8,789,737 B2 | 7/2014 | Hodgkinson et al. |
| 8,814,888 B2 | 8/2014 | Sgro |
| 8,820,606 B2 | 9/2014 | Hodgkinson |
| 8,827,133 B2 | 9/2014 | Shelton, IV et al. |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |
| 8,920,443 B2 | 12/2014 | Hiles et al. |
| 8,920,444 B2 | 12/2014 | Hiles et al. |
| 8,939,344 B2 | 1/2015 | Olson et al. |
| 8,956,390 B2 | 2/2015 | Shah et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | Stopek et al. |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 * | 6/2015 | Hodgkinson ...... A61B 17/3211 |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,871 B2 | 8/2015 | Milliman et al. |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,140 B2 | 11/2015 | Hiles et al. |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 * | 12/2015 | Viola ................ A61B 17/064 |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,768 B2 | 5/2016 | Shelton, IV |
| 9,326,773 B2 | 5/2016 | Casasanta, Jr. et al. |
| 9,328,111 B2 | 5/2016 | Zhou et al. |
| 9,345,479 B2 | 5/2016 | Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,358,005 B2 | 6/2016 | Shelton, IV et al. |
| 9,364,229 B2 | 6/2016 | D'Agostino et al. |
| 9,364,234 B2 | 6/2016 | Stopek et al. |
| 9,386,988 B2 | 7/2016 | Baxter, III et al. |
| 9,402,627 B2 | 8/2016 | Stevenson et al. |
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,463,260 B2 | 10/2016 | Stopek |
| 9,486,215 B2 | 11/2016 | Olson et al. |
| 9,492,170 B2 | 11/2016 | Bear et al. |
| 9,504,470 B2 | 11/2016 | Milliman |
| 9,517,164 B2 | 12/2016 | Vitaris et al. |
| 9,572,576 B2 | 2/2017 | Hodgkinson et al. |
| 9,585,657 B2 | 3/2017 | Shelton, IV et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,629,626 B2 | 4/2017 | Soltz et al. |
| 9,636,850 B2 | 5/2017 | Stopek et al. |
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 9,687,262 B2 | 6/2017 | Rousseau et al. |
| 9,693,772 B2 | 7/2017 | Ingmanson et al. |
| 9,708,184 B2 | 7/2017 | Chan et al. |
| 9,770,245 B2 | 9/2017 | Swayze et al. |
| 9,775,617 B2 | 10/2017 | Carter et al. |
| 9,775,618 B2 | 10/2017 | Bettuchi et al. |
| 9,782,173 B2 | 10/2017 | Mozdzierz |
| 9,844,378 B2 | 12/2017 | Casasanta et al. |
| 9,918,713 B2 | 3/2018 | Zergiebel et al. |
| 9,931,116 B2 | 4/2018 | Racenet et al. |
| 10,022,125 B2 | 7/2018 | Stopek et al. |
| 10,098,639 B2 | 10/2018 | Hodgkinson |
| 10,111,659 B2 | 10/2018 | Racenet et al. |
| 10,154,840 B2 | 12/2018 | Viola et al. |
| 11,141,151 B2 | 10/2021 | Kollar et al. |
| 2002/0091397 A1 | 7/2002 | Chen |
| 2002/0151911 A1 | 10/2002 | Gabbay |
| 2003/0065345 A1 | 4/2003 | Weadock |
| 2003/0078209 A1 | 4/2003 | Schmidt |
| 2003/0083676 A1 | 5/2003 | Wallace |
| 2003/0125676 A1 | 7/2003 | Swenson et al. |
| 2003/0181927 A1 | 9/2003 | Wallace |
| 2003/0183671 A1 | 10/2003 | Mooradian et al. |
| 2003/0208231 A1 | 11/2003 | Williamson et al. |
| 2004/0092912 A1 | 5/2004 | Jinno et al. |
| 2004/0107006 A1 | 6/2004 | Francis et al. |
| 2004/0131418 A1 | 7/2004 | Budde et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |
| 2005/0059996 A1 | 3/2005 | Bauman et al. |
| 2005/0059997 A1 * | 3/2005 | Bauman ............... A61B 17/072 606/219 |
| 2005/0070929 A1 | 3/2005 | Dalessandro et al. |
| 2005/0118435 A1 | 6/2005 | DeLucia et al. |
| 2005/0149073 A1 | 7/2005 | Arani et al. |

(56) References Cited

U.S. PATENT DOCUMENTS

| | | |
|---|---|---|
| 2005/0245965 A1 | 11/2005 | Orban, III et al. |
| 2005/0283256 A1 | 12/2005 | Sommerich et al. |
| 2006/0008505 A1 | 1/2006 | Brandon |
| 2006/0121266 A1 | 6/2006 | Fandel et al. |
| 2006/0173470 A1 | 8/2006 | Oray et al. |
| 2006/0190027 A1 | 8/2006 | Downey |
| 2007/0034669 A1 | 2/2007 | De La Torre et al. |
| 2007/0203510 A1 | 8/2007 | Bettuchi |
| 2007/0243227 A1 | 10/2007 | Gertner |
| 2007/0246505 A1 | 10/2007 | Pace-Floridia et al. |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0140115 A1 | 6/2008 | Stopek |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0216855 A1 | 9/2008 | Nasca |
| 2008/0220047 A1 | 9/2008 | Sawhney et al. |
| 2008/0290134 A1 | 11/2008 | Bettuchi et al. |
| 2009/0001121 A1 | 1/2009 | Hess et al. |
| 2009/0001130 A1 | 1/2009 | Hess et al. |
| 2009/0031842 A1 | 2/2009 | Kawai et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0218384 A1 | 9/2009 | Aranyi |
| 2009/0277944 A9 | 11/2009 | Dalessandro et al. |
| 2010/0016855 A1 | 1/2010 | Ramstein et al. |
| 2010/0016888 A1 | 1/2010 | Calabrese et al. |
| 2010/0087840 A1 | 4/2010 | Ebersole et al. |
| 2010/0147921 A1 | 6/2010 | Olson |
| 2010/0147922 A1 | 6/2010 | Olson |
| 2010/0174253 A1 | 7/2010 | Cline et al. |
| 2010/0203151 A1 | 8/2010 | Hiraoka |
| 2010/0243707 A1 | 9/2010 | Olson et al. |
| 2010/0331859 A1 | 12/2010 | Omori |
| 2011/0034910 A1 | 2/2011 | Ross et al. |
| 2011/0089220 A1 | 4/2011 | Ingmanson et al. |
| 2011/0125138 A1 | 5/2011 | Malinouskas et al. |
| 2011/0166673 A1 | 7/2011 | Patel et al. |
| 2011/0278346 A1 | 11/2011 | Hull et al. |
| 2011/0293690 A1 | 12/2011 | Griffin et al. |
| 2012/0080336 A1 | 4/2012 | Shelton, IV et al. |
| 2012/0197272 A1 | 8/2012 | Oray et al. |
| 2012/0241491 A1 | 9/2012 | Aldridge et al. |
| 2012/0241493 A1 | 9/2012 | Baxter, III et al. |
| 2012/0253298 A1 | 10/2012 | Henderson et al. |
| 2013/0153634 A1 | 6/2013 | Carter et al. |
| 2013/0153636 A1 | 6/2013 | Shelton, IV et al. |
| 2013/0153638 A1 | 6/2013 | Carter et al. |
| 2013/0153639 A1 | 6/2013 | Hodgkinson et al. |
| 2013/0153641 A1 | 6/2013 | Shelton, IV et al. |
| 2013/0193191 A1 | 8/2013 | Stevenson et al. |
| 2013/0193192 A1* | 8/2013 | Casasanta, Jr. ...... A61B 17/068 227/180.1 |
| 2013/0256380 A1 | 10/2013 | Schmid et al. |
| 2014/0048580 A1 | 2/2014 | Merchant et al. |
| 2014/0097224 A1* | 4/2014 | Prior ................ A61B 17/07292 227/176.1 |
| 2014/0131418 A1 | 5/2014 | Kostrzewski |
| 2014/0224686 A1 | 8/2014 | Aronhalt et al. |
| 2014/0239046 A1* | 8/2014 | Milliman ......... A61B 17/07292 227/176.1 |
| 2014/0239047 A1 | 8/2014 | Hodgkinson et al. |
| 2014/0252062 A1 | 9/2014 | Mozdzierz |
| 2015/0041347 A1 | 2/2015 | Hodgkinson |
| 2015/0133995 A1 | 5/2015 | Shelton, IV et al. |
| 2015/0157320 A1 | 6/2015 | Zergiebel et al. |
| 2015/0157321 A1 | 6/2015 | Zergiebel et al. |
| 2015/0209045 A1 | 7/2015 | Hodgkinson et al. |
| 2015/0231409 A1 | 8/2015 | Racenet et al. |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0100834 A1 | 4/2016 | Viola et al. |
| 2016/0106430 A1 | 4/2016 | Carter et al. |
| 2016/0128694 A1 | 5/2016 | Baxter, III et al. |
| 2016/0157857 A1 | 6/2016 | Hodgkinson et al. |
| 2016/0174988 A1 | 6/2016 | D'Agostino et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0270793 A1 | 9/2016 | Carter et al. |
| 2016/0310143 A1 | 10/2016 | Bettuchi |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0119390 A1 | 5/2017 | Schellin et al. |
| 2017/0150967 A1 | 6/2017 | Hodgkinson et al. |
| 2017/0172575 A1 | 6/2017 | Hodgkinson |
| 2017/0231629 A1 | 8/2017 | Stopek et al. |
| 2017/0238931 A1 | 8/2017 | Prescott et al. |
| 2017/0281182 A1* | 10/2017 | Nativ ................ A61B 17/1155 |
| 2017/0281328 A1 | 10/2017 | Hodgkinson et al. |
| 2017/0296188 A1 | 10/2017 | Ingmanson et al. |
| 2017/0354415 A1 | 12/2017 | Casasanta, Jr. et al. |
| 2018/0125491 A1 | 5/2018 | Aranyi |
| 2018/0140301 A1 | 5/2018 | Milliman |
| 2018/0168654 A1 | 6/2018 | Hodgkinson et al. |
| 2018/0214147 A1 | 8/2018 | Merchant et al. |
| 2018/0229054 A1 | 8/2018 | Racenet et al. |
| 2018/0250000 A1 | 9/2018 | Hodgkinson et al. |
| 2018/0256164 A1 | 9/2018 | Aranyi |
| 2018/0296214 A1 | 10/2018 | Hodgkinson et al. |
| 2018/0310937 A1 | 11/2018 | Stopek et al. |
| 2019/0021734 A1 | 1/2019 | Hodgkinson |
| 2019/0059878 A1 | 2/2019 | Racenet et al. |
| 2019/0083087 A1 | 3/2019 | Viola et al. |

FOREIGN PATENT DOCUMENTS

| | | |
|---|---|---|
| DE | 19924311 A1 | 11/2000 |
| EP | 0327022 A2 | 8/1989 |
| EP | 0594148 A1 | 4/1994 |
| EP | 2491867 A1 | 8/2012 |
| JP | 2000166933 A | 6/2000 |
| JP | 2002202213 A | 7/2002 |
| JP | 2007124166 A | 5/2007 |
| JP | 2010214132 A | 9/2010 |
| WO | 9005489 A1 | 5/1990 |
| WO | 9516221 A1 | 6/1995 |
| WO | 9838923 A1 | 9/1998 |
| WO | 9926826 A2 | 6/1999 |
| WO | 0010456 A1 | 3/2000 |
| WO | 0016684 A1 | 3/2000 |
| WO | 2010075298 A2 | 7/2010 |

OTHER PUBLICATIONS

Extended European Search Report corresponding to EP 17 17 8528.0 dated Oct. 13, 2017.
Australian Examination Report No. 1 corresponding to AU 2013234420 dated Oct. 24, 2017.
Japanese Office Action corresponding to JP 2013-175379 dated Oct. 20, 2017.
Japanese Office Action corresponding to JP 2013-147701 dated Oct. 27, 2017.
Extended European Search Report corresponding to EP 17 17 5656.2 dated Nov. 7, 2017.
Japanese Office Action corresponding to JP 2014-009738 dated Nov. 14, 2017.
European Office Action corresponding to EP 13 17 3986.4 dated Nov. 29, 2017.
Japanese Office Action corresponding to JP 2017-075975 dated Dec. 4, 2017.

(56) References Cited

OTHER PUBLICATIONS

European Office Action corresponding to EP 13 19 7958.5 dated Dec. 11, 2017.
Chinese First Office Action corresponding to Patent Application CN 201410588811.8 dated Dec. 5, 2017.
European Office Action corresponding to Patent Application EP 16 16 6367.9 dated Dec. 11, 2017.
Chinese First Office Action corresponding to Patent Application ON 201610279682.3 dated Jan. 10, 2018.
Japanese Office Action corresponding to Patent Application JP 2013-154561 dated Jan. 15, 2018.
Australian Examination Report No. 1 corresponding to Patent Application AU 2017225037 dated Jan. 23, 2018.
Japanese Office Action corresponding to Patent Application JP 2013-229471 dated May 1, 2018.
Canadian Office Action corresponding to Patent Application CA 2,790,743 dated May 14, 2018.
European Office Action corresponding to Patent Application EP 14 15 7195.0 dated Jun. 12, 2018.
European Office Action corresponding to EP 14 17 2681.0 dated May 13, 2016.
Extended European Search Report corresponding to EP 16 15 3647.9 dated Jun. 3, 2016.
Chinese Office Action corresponding to CN 201210545228 dated Jun. 29, 2016.
Japanese Office Action corresponding to JP 2012-250058 dated Jun. 29, 2016.
European Office Action corresponding to EP 14 15 7997.9 dated Jun. 29, 2016.
Canadian Office Action corresponding to CA 40002,712,617 dated Jun. 30, 2016.
Chinese First Office Action corresponding to CN 2013103036903 dated Jun. 30, 2016.
Australian Patent Examination Report No. 1 corresponding to AU 2012250278 dated Jul. 10, 2016.
Australian Patent Examination Report No. 1 corresponding to AU 2012244382 dated Jul. 10, 2016.
Japanese Office Action corresponding to 2012-255242 dated Jul. 26, 2016.
Japanese Office Action corresponding to JP 2012-268668 dated Jul. 27, 2016.
European Office Action corresponding to EP 14 15 2060.1 dated Aug. 4, 2016.
European Office Action corresponding to EP 12 16 5609.4 dated Aug. 5, 2016.
European Office Action corresponding to EP 15 15 2392.5 dated Aug. 8, 2016.
Japanese Office Action corresponding to JP 2013-003624 dated Aug. 25, 2016.
Australian Patent Examination Report No. 1 corresponding to AU 2012261752 dated Sep. 6, 2016.
Japanese Office Action corresponding to JP 2014-252703 dated Sep. 26, 2016.
European Office Action corresponding to EP 12 19 8776.2 dated Sep. 12, 2016.
Japanese Office Action corresponding to JP 2013-000321 dated Sep. 13, 2016.
Chinese Second Office Action corresponding to CN 201310353628.5 dated Sep. 26, 2016.
European Office Action corresponding to EP 12 15 2541.4 dated Sep. 27, 2016.
Australian Patent Examination Report No. 1 corresponding to AU 2012268923 dated Sep. 28, 2016.
Chinese First Office Action corresponding to CN 2013107068710 dated Dec. 16, 2016.
Chinese First Office Action corresponding to CN 201310646606.8 dated Dec. 23, 2016.
Japanese Office Action corresponding to JP 2013-000321 dated Jan. 4, 2017.
Extended European Search Report corresponding to EP 16 16 6367.9 dated Jan. 16, 2017.
Australian Examination Report No. 1 corresponding to AU 2013206777 dated Feb. 1, 2017.
Chinese Second Office Action corresponding to CN 2013103036903 dated Feb. 23, 2017.
Japanese Office Action corresponding to JP 2013-175379 dated Mar. 1, 2017.
Chinese First Office Action corresponding to CN 201410028462.4 dated Mar. 2, 2017.
Chinese First Office Action corresponding to CN 201410084070 dated Mar. 13, 2017.
Extended European Search Report corresponding to EP 16 19 6549.6 dated Mar. 17, 2017.
Japanese Office Action corresponding to JP 2013-147701 dated Mar. 21, 2017.
Australian Examination Report No. 1 corresponding to AU 2013206804 dated Mar. 21, 2017.
Australian Examination Report No. 1 corresponding to AU 2013211499 dated May 4, 2017.
Australian Examination Report No. 1 corresponding to AU 2014201008 dated May 23, 2017.
European Office Action corresponding to EP 15 17 4146.9 dated May 15, 2017.
Japanese Office Action corresponding to JP 2013-154561 dated May 23, 2017.
European Office Action corresponding to EP 12 19 4784.0 dated May 29, 2017.
Japanese Office Action corresponding to JP 2013-169083 dated May 31, 2017.
Australian Examination Report No. 1 corresponding to AU 2013213767 dated Jun. 29, 2017.
Australian Examination Report No. 2 corresponding to AU 2012261752 dated Jul. 7, 2017.
Australian Examination Report No. 1 corresponding to AU 2013266989 dated Jul. 10, 2017.
Extended European Search Report corresponding to EP 14 15 3609.4 dated Jul. 14, 2017.
Australian Examination Report No. 1 corresponding to AU 2013234418 dated Jul. 14, 2017.
Extended European Search Report corresponding to EP 14 15 3610.2 dated Jul. 17, 2017.
Australian Examination Report No. 1 corresponding to AU 2014200109 dated Jul. 20, 2017.
Australian Examination Report No. 1 corresponding to AU 2014200074 dated Jul. 20, 2017.
Japanese Office Action corresponding to JP 2013-250857 dated Aug. 17, 2017.
Japanese Office Action corresponding to JP 2013-229471 dated Aug. 17, 2017.
Extended European Search Report dated Apr. 25, 2019 corresponding to counterpart Patent Application EP 18210979.3.
Extended European Search Report corresponding to Patent Application EP 12196912.5 dated Feb. 1, 2016.
Chinese Second Office Action corresponding to Patent Application CN 201610279682.3 dated Aug. 8, 2018.
Chinese Second Office Action corresponding to Patent Application CN 201410588811.8 dated Aug. 27, 2018.
Extended European Search Report corresponding to Patent Application EP 18160809.2 dated Sep. 18, 2018.
Extended European Search Report corresponding to Patent Application EP 18192317.8 dated Dec. 20, 2018.
Extended European Search Report corresponding to Patent Application EP 18190154.7 dated Feb. 4, 2019.
Extended European Search Report corresponding to EP 14 16 9739.1, completed Aug. 19, 2014 and Aug. 29, 2014; (7 pp).
Extended European Search Report corresponding to EP 14 15 7997.9, completed Sep. 9, 2014 and dated Sep. 17, 2014; (8 pp).
Extended European Search Report corresponding to EP 14 16 8904.2, completed Sep. 10, 2014 and dated Sep. 18, 2014; (8 pp).
Extended European Search Report corresponding to EP 13 19 4995.0, completed Jun. 5, 2014 and dated Oct. 13, 2014; (10 pp).

(56) References Cited

OTHER PUBLICATIONS

Extended European Search Report corresponding to EP 13 15 4571.7, completed Oct. 10, 2014 and dated Oct. 20, 2014; (8 pp).
Extended European Search Report corresponding to EP 14 18 1125.7, completed Oct. 16, 2014 and dated Oct. 24, 2014; (7 pp).
Extended European Search Report corresponding to EP 14 18 1127.3, completed Oct. 16, 2014 and dated Nov. 10, 2014; (8 pp).
Extended European Search Report corresponding to EP 14 19 0419.3, completed Mar. 24, 2015 and dated Mar. 30, 2015; (6 pp).
European Office Action corresponding to EP 12 198 776.2 dated Apr. 7, 2015.
European Office Action corresponding to EP 13 156 297.7 dated Apr. 10, 2015.
Australian Examination Report No. 1 corresponding to AU 2011250822 dated May 18, 2015.
European Office Action corresponding to EP 12 186 175.1 dated Jun. 1, 2015.
Chinese Office Action corresponding to CN 201010517292.8 dated Jun. 2, 2015.
Extended European Search Report corresponding to EP 14 17 4814.5 dated Jun. 9, 2015.
Australian Examination Report No. 1 corresponding to AU 2014200584 dated Jun. 15, 2015.
European Office Action corresponding to EP 13 180 881.8 dated Jun. 19, 2015.
European Office Action corresponding to EP 14 157 195.0 dated Jul. 2, 2015.
Extended European Search Report corresponding to EP 12 19 6902.6 dated Aug. 6, 2015.
Extended European Search Report corresponding to EP 14 15 2060.1 dated Aug. 14, 2015.
Chinese Office Action corresponding to CN 201210129787.2 dated Aug. 24, 2015.
Canadian Office Action corresponding to CA 2,665,206 dated Nov. 19, 2013.
Chinese Notification of Reexamination corresponding to CN 201010517292.8 dated Jun. 2, 2015.
Japanese Office Action corresponding to JP 2014-216989 dated Sep. 11, 2015.
Canadian First Office Action corresponding to CA 2,686,105 dated Sep. 17, 2015.
Japanese Office Action corresponding to JP 2012-040188 dated Oct. 21, 2015.
European Search Report corresponding to EP 06 00 4598, completed Jun. 22, 2006; (2 pp).
European Search Report corresponding to EP 06 01 6962.0, completed Jan. 3, 2007 and dated Jan. 11, 2007; (10 pp).
International Search Report corresponding to International Application No. PCT/US2005/036740, completed Feb. 20, 2007 and dated Mar. 23, 2007; (8 pp).
International Search Report corresponding to International Application No. PCT/US2007/022713, completed Apr. 21, 2008 and dated May 15, 2008; (1 p).
International Search Report corresponding to International Application No. PCT/US2008/002981, completed Jun. 9, 2008 and dated Jun. 26, 2008; (2 pp).
European Search Report corresponding to EP 08 25 1779, completed Jul. 14, 2008 and dated Jul. 23, 2008; (5 pp).
European Search Report corresponding to EP 08 25 1989.3, completed Mar. 11, 2010 and dated Mar. 24, 2010; (6 pp).
European Search Report corresponding to EP 10 25 0639.1, completed Jun. 17, 2010 and dated Jun. 28, 2010; (7 pp).
European Search Report corresponding to EP 10 25 0715.9, completed Jun. 30, 2010 and dated Jul. 20, 2010; (3 pp).
European Search Report corresponding to EP 05 80 4382.9, completed Oct. 5, 2010 and dated Oct. 12, 2010; (3 pp).
European Search Report corresponding to EP 09 25 2897.5, completed Feb. 7, 2011 and dated Feb. 15, 2011; (3 pp).
European Search Report corresponding to EP 10 25 0642.5, completed Mar. 25, 2011 and dated Apr. 4, 2011; (4 pp).
European Search Report corresponding to EP 12 15 2229.6, completed Feb. 23, 2012 and dated Mar. 1, 2012; (4 pp).
European Search Report corresponding to EP 12 15 0511.9, completed Apr. 16, 2012 and dated Apr. 24, 2012; (7 pp).
European Search Report corresponding to EP 12 15 2541.4, completed Apr. 23, 2012 and dated May 3, 2012; (10 pp).
European Search Report corresponding to EP 12 16 5609.4, completed Jul. 5, 2012 and dated Jul. 13, 2012; (8 pp).
European Search Report corresponding to EP 12 15 8861.0, completed Jul. 17, 2012 and dated Jul. 24, 2012; (9 pp).
European Search Report corresponding to EP 12 16 5878.5, completed Jul. 24, 2012 and dated Aug. 6, 2012; (8 pp).
Extended European Search Report corresponding to EP 12 19 1035.0, completed Jan. 11, 2013 and dated Jan. 18, 2013; (7 pp).
Extended European Search Report corresponding to EP 12 18 6175.1, completed Jan. 15, 2013 and dated Jan. 23, 2013; (7 pp).
Extended European Search Report corresponding to EP 12 19 1114.3, completed Jan. 23, 2013 and dated Jan. 31, 2013; (10 pp).
Extended European Search Report corresponding to EP 12 19 2224.9, completed Mar. 14, 2013 and dated Mar. 26, 2013; (8 pp).
Extended European Search Report corresponding to EP 12 19 6904.2, completed Mar. 28, 2013 and dated Jul. 26, 2013; (8 pp).
Extended European Search Report corresponding to EP 12 19 6911.7, completed Apr. 18, 2013 and dated Apr. 24, 2013; (8 pp).
Extended European Search Report corresponding to EP 07 00 5842.5, completed May 13, 2013 and dated May 29, 2013; (7 pp).
Extended European Search Report corresponding to EP 12 19 8776.2, completed May 16, 2013 and dated May 27, 2013; (8 pp).
Extended European Search Report corresponding to EP 12 19 8749.9, completed May 21, 2013 and dated May 31, 2013; (8 pp).
Extended European Search Report corresponding to EP 13 15 6297.7, completed Jun. 4, 2013 and dated Jun. 13, 2013; (7 pp).
Extended European Search Report corresponding to EP 13 17 3985.6, completed Aug. 19, 2013 and dated Aug. 28, 2013; (6 pp).
Extended European Search Report corresponding to EP 13 17 3986.4, completed Aug. 20, 2013 and dated Aug. 29, 2013; (6 pp).
Extended European Search Report corresponding to EP 13 17 7437.4, completed Sep. 11, 2013 and dated Sep. 19, 2013; 6 pages.
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 18 2911.1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
Extended European Search Report corresponding to EP 13 19 2111.6, completed Feb. 13, 2014 and dated Feb. 27, 2014; (10 pp).
Extended European Search Report corresponding to EP 13 19 5919.9, completed Feb. 10, 2014 and dated Mar. 3, 2014; (7 pp).
Extended European Search Report corresponding to EP 08 72 6500.5, completed Feb. 20, 2014 and dated Mar. 3, 2014; (7 pp).
Extended European Search Report corresponding to EP 13 19 5019.8, completed Mar. 14, 2014 and dated Mar. 24, 2014; (7 pp).
Extended European Search Report corresponding to EP 13 19 6816.6, completed Mar. 28, 2014 and dated Apr. 9, 2014; (9 pp).
Extended European Search Report corresponding to EP 13 19 7958.5, completed Apr. 4, 2014 and dated Apr. 15, 2014; (8 pp).
Extended European Search Report corresponding to EP 13 19 4995.0, completed Jun. 5, 2014 and dated Jun. 16, 2014; (5 pp).

(56) References Cited

OTHER PUBLICATIONS

Extended European Search Report corresponding to EP 14 15 7195.0, completed Jun. 5, 2014 and dated Jun. 18, 2014; (9 pp).
Extended European Search Report corresponding to EP 14 15 6342.9, completed Jul. 22, 2014 and dated Jul. 29, 2014; (8 pp).
European Communication corresponding to EP 13 17 6895.4 dated Nov. 5, 2015.
Chinese First Office Action corresponding to CN 201210544552 dated Nov. 23, 2015.
Chinese First Office Action corresponding to CN 201210545228 dated Nov. 30, 2015.
Extended European Search Report corresponding to EP 15 18 0491.1 dated Dec. 9, 2015.
Extended European Search Report corresponding to EP 15 18 3819.0 dated Dec. 11, 2015.
Canadian Office Action corresponding to CA 2,697,819 dated Jan. 6, 2016.
Canadian Office Action corresponding to CA 2,696,419 dated Jan. 14, 2016.
European Office Action corresponding to EP 12 19 8776.2 dated Jan. 19, 2016.
Extended European Search Report corresponding to EP 15 17 4146.9 dated Jan. 20, 2016.
Chinese First Office Action corresponding to CN 201310353628.5 dated Jan. 25, 2016.
Extended European Search Report corresponding to EP 12 19 6912.5 dated Feb. 1, 2016.
Japanese Office Action corresponding to JP 2012-098903 dated Feb. 22, 2016.
Extended European Search Report corresponding to EP 12 19 8753.1 dated Feb. 24, 2016.
Chinese First Office Action corresponding to CN 201410449019.4 dated Mar. 30, 2016.
Extended European Search Report corresponding to EP 16 15 0232.3 dated Apr. 12, 2016.
European Office Action corresponding to EP 11 18 3256.4 dated Apr. 20, 2016.
Australian Examination Report No. 1 corresponding to AU 2012244169 dated May 10, 2016.
European Office Action corresponding to EP 10 25 0715.9 dated May 12, 2016.
Chinese First Office Action corresponding to CN 201410778512.0 dated May 13, 2016.
Australian Examination Report No. 1 corresponding to AU 2012227358 dated May 16, 2016.
Japanese Office Action corresponding to JP 2012-040188 dated May 17, 2016.
Australian Examination Report No. 1 corresponding to AU 2012244380 dated May 20, 2016.
Australian Examination Report No. 1 corresponding to AU 2014227480 dated May 21, 2016.
Australian Examination Report No. 1 corresponding to AU 2012254977 dated May 30, 2016.

* cited by examiner

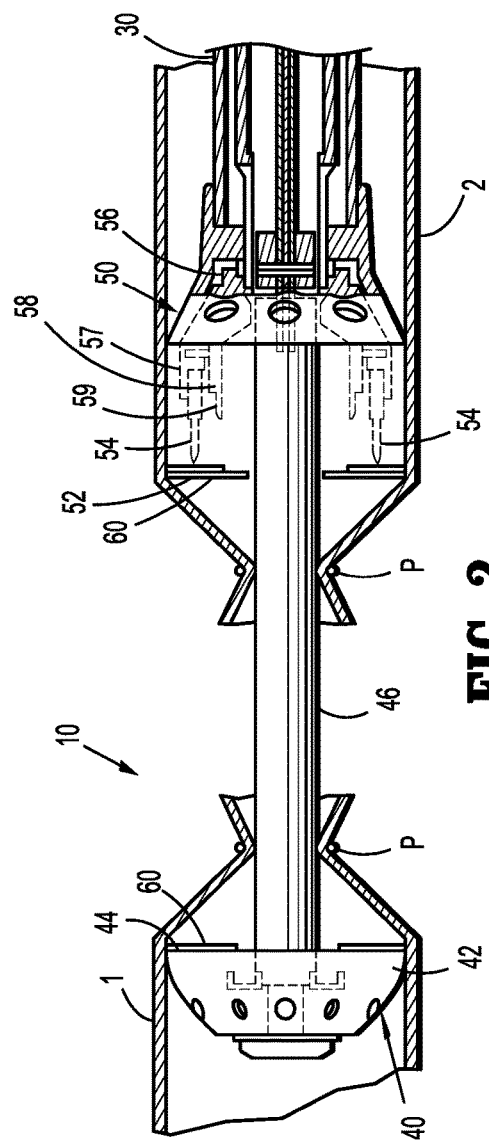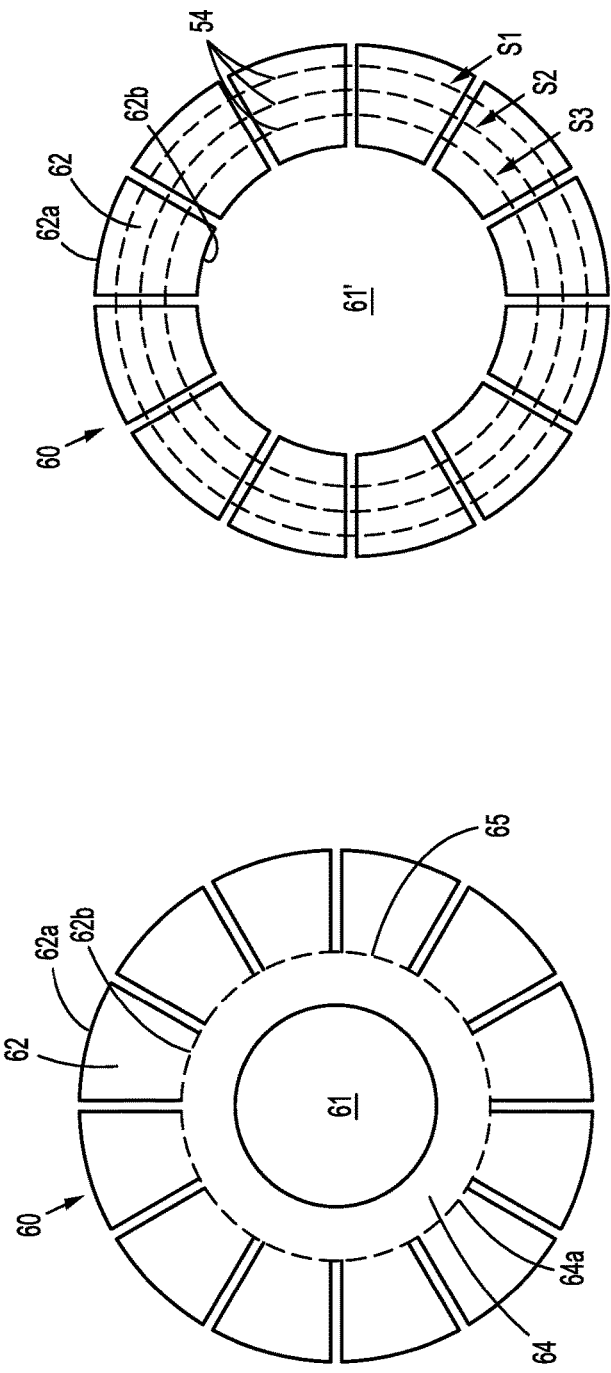
FIG. 2
FIG. 3A
FIG. 3B

SURGICAL BUTTRESS FOR CIRCULAR STAPLING

CROSS-REFERENCE TO RELATED APPLICATION

This application is a continuation of U.S. patent application Ser. No. 16/189,601, filed Nov. 13, 2018 (now U.S. Pat. No. 11,141,151), which claims the benefit of and priority to U.S. Provisional Patent Application No. 62/596,146, filed Dec. 8, 2017, the entire disclosure of each of which is incorporated by reference herein.

BACKGROUND

Technical Field

The present disclosure relates to surgical buttresses that are releasably attached to surgical stapling apparatus and more particularly, to surgical buttresses for flexibly reinforcing circular staples lines.

Description of Related Art

Surgical stapling apparatus are employed by surgeons to sequentially or simultaneously apply one or more rows of fasteners, e.g., staples or two-part fasteners, to body tissue for the purpose of joining segments of body tissue together and/or creating anastomoses.

Annular surgical stapling apparatus generally include a staple cartridge assembly including annular rows of staples, an anvil assembly operatively associated with the staple cartridge assembly, and an annular blade disposed internal to the annular rows of staples. In use, during an end-to-end circular anastomosis procedure, two ends of hollow tissue sections, e.g., bowels, intestines, or other tubular organs) are clamped between the anvil and staple cartridge assemblies and are joined by driving the annular rows of staples through the clamped hollow tissue sections. During firing of the staples, the annular blade is advanced to cut portions of the tissue sections extending inside the staple lines, thereby establishing a passage through the two stapled tissue sections.

Surgical supports, e.g., meshes or buttress materials, may be used in combination with surgical stapling apparatus to bridge, repair, and/or reinforce tissue defects within a patient. The surgical support reinforces the staple line as well as covers the juncture of the tissues to reduce incidents of, for example, tearing, leakage, bleeding, and/or strictures prior to healing. The staple lines, however, may become rigid with the addition of the surgical support which may affect removal of the anvil assembly through the stapled tissue and/or affect the staple lines themselves. Accordingly, a need exists for improved surgical supports and/or buttresses.

SUMMARY

The present disclosure is directed to surgical buttresses including discrete body segments for reinforcing staple lines while maintaining flexibility of the tissue to which the surgical buttress is attached.

A surgical stapling apparatus, including a releasable surgical buttress, in accordance with aspects of the present disclosure, includes a staple cartridge assembly, an anvil assembly operatively associated with the staple cartridge assembly, and a surgical buttress. The staple cartridge assembly includes a tissue facing surface having staple retaining slots defined therein, each staple retaining slot housing a staple therein, and an annular knife disposed radially inwardly of the tissue facing surface. The anvil assembly includes an anvil member including a tissue facing surface having staple forming recesses defined therein, and an anvil shaft extending from the anvil member. The surgical buttress is disposed on the tissue facing surface of the staple cartridge assembly or the anvil assembly. The surgical buttress has an annular configuration defining a central aperture therethrough, and includes body segments extending radially outwardly about the central aperture in spaced radial relation relative to each other, and a ring segment interconnecting the body segments.

An adhesive may be disposed between the surgical buttress and the tissue facing surface of the staple cartridge assembly or the anvil assembly to releasably retain the surgical buttress thereon. The surgical buttress may include eight to fourteen body segments. The central aperture of the surgical buttress may have a diameter that is larger than a diameter of the anvil shaft of the anvil assembly. The surgical buttress may include perforations disposed between the body segments and the ring segment.

In embodiments, a portion of the body segments of the surgical buttress are formed from a first material and a portion of the body segments of the surgical buttress are formed from a second material. The body segments formed from the first material and the body segments formed from the second material may be alternately positioned around the central aperture. In some embodiments, the body segments and the ring segment of the surgical buttress are formed from different materials.

The ring segment of the surgical buttress may extend radially inwardly from radial inner edges of the body segments. The ring segment of the surgical buttress may be positioned radially inwardly of the annular knife of the staple cartridge assembly. In embodiments, a radial outer edge of the ring segment is radially aligned with the annular knife of the staple cartridge assembly such that actuation of the knife severs the ring segment from the body segments. In some embodiments, radial outer edges of the body segments define a radial outer terminal edge of the surgical buttress. In certain embodiments, the surgical buttress includes a second ring segment positioned radially outwardly of the annular knife of the staple cartridge assembly.

The ring segment of the surgical buttress may extend radially outwardly from radial outer edges of the body segments. The ring segment of the surgical buttress may be positioned radially outwardly of the annular knife of the staple cartridge assembly. In embodiments, a radial outer edge of the ring segment of the surgical buttress defines a radial outer terminal edge of the surgical buttress. In some embodiments, radial inner edges of the body segments of the surgical buttress define a radial inner terminal edge of the surgical buttress. The radial inner edges of the body segments may be aligned with a radial inner perimeter of the tissue facing surface of the anvil assembly or the staple cartridge assembly. In certain embodiments, a radial outer edge of the ring segment is aligned with a radial outer perimeter of the tissue facing surface of the anvil assembly or the staple cartridge assembly. The ring segment of the surgical buttress may be disposed over at least one annular row of the staple forming recesses or the staple forming slots of the anvil assembly or the staple cartridge assembly to which the surgical buttress is releasably secured.

A staple cartridge assembly including a releasable surgical buttress, in accordance with aspects of the present disclosure, includes a staple cartridge including a tissue facing surface having staple retaining slots defined therein, each staple retaining slot housing a staple therein, and an annular knife disposed radially inwardly of the tissue facing surface. The surgical buttress is disposed on the tissue facing surface of the staple cartridge assembly. The surgical buttress has an annular configuration defining a central aperture therethrough, and includes body segments extending radially outwardly about the central aperture in spaced radial relation relative to each other, and a ring segment interconnecting the body segments.

Other aspects, features, and advantages will be apparent from the description, drawings, and the claim.

BRIEF DESCRIPTION OF THE DRAWINGS

Various aspects of the present disclosure are described herein below with reference to the drawings, which are incorporated in and constitute a part of this specification, wherein:

FIG. 2 is a partial cross-sectional view of the surgical stapling apparatus shown in FIG. 1A, including surgical buttresses releasably attached thereto in accordance with an embodiment of the present disclosure;

FIG. 3A is a top, plan view of a surgical buttress of FIG. 2, in an initial configuration prior to actuation of the surgical stapling apparatus;

FIG. 3B is a top, plan view of the surgical buttress of FIG. 3A, in a final configuration after actuation of the surgical stapling apparatus;

DETAILED DESCRIPTION

Figure 1B:
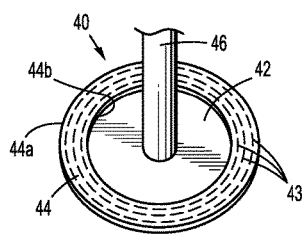
FIG. 1B is a bottom, perspective view of an anvil assembly of the surgical stapling apparatus of FIG. 1A.

Various exemplary embodiments of the present disclosure are discussed herein below in terms of surgical buttresses for use with a surgical stapling apparatus. The surgical buttresses described herein may be used in sealing a wound by approximating the edges of tissue between a staple cartridge assembly and an anvil assembly of the surgical stapling apparatus which includes at least one surgical buttress. The surgical buttress is releasably attached to the surgical stapling apparatus such that staples fired from the surgical stapling apparatus attach the surgical buttress to tissue.

Embodiments of the presently disclosed surgical buttresses will now be described in detail with reference to the drawing figures wherein like reference numerals identify similar or identical elements. Throughout this description, the term "proximal" refers to a portion of a structure, or component thereof, that is closer to a user, and the term "distal" refers to a portion of the structure, or component thereof, that is farther from the user. Directional reference terms, such as "top," "bottom," "side," and the like, are intended to ease description of the embodiments and are not intended to have any limiting effect on the ultimate orientations of a structure or any parts thereof.

Figure 1A:
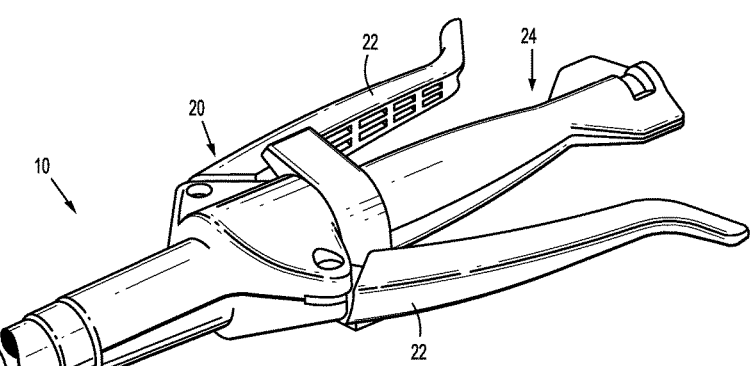
FIG. 1A is a side, perspective view of a surgical stapling apparatus in accordance with an embodiment of the present disclosure.

Referring now to FIG. 1A, a surgical stapling apparatus or circular stapler 10 for use in stapling tissue and applying a surgical buttress to tissue is shown. The surgical stapling apparatus 10 includes a handle assembly 20, an elongated tubular body 30 extending distally from the handle assembly 20, an anvil assembly 40 releasably coupled to a distal end portion 32 of the elongated tubular body 20, and a staple cartridge assembly 50 disposed at the distal end portion 32 of the elongated tubular body 30.

The handle assembly 20 includes at least one movable handle member 22 for actuating the firing of staples 54 (FIG. 2) from the staple cartridge assembly 50 and the cutting of tissue secured between the anvil and staple cartridge assemblies 40, 50. The handle assembly 20 further includes an advancing member 24 for moving the anvil assembly 40 between an open or spaced apart position and a closed or approximated position relative to the staple cartridge assembly 50.

The elongated tubular body 30 may be flexible or rigid, and/or straight or curved along a portion or the entirety thereof. It should be understood that the elongated tubular body 30 may be otherwise configured (e.g., shaped and/or dimensioned) depending on, for example, the surgical application or procedure of use as is within the purview of those skilled in the art. The staple cartridge assembly 50 may be fixedly connected to the distal end portion 32 of the elongated tubular body 30 or may be configured to concentrically fit within, or be otherwise connected to, the distal end portion 32 of the elongated tubular body 30 such that the staple cartridge assembly 50 is removable and replaceable.

As shown in FIGS. 1A and 1B, the anvil assembly 40 includes an anvil member 42 having a tissue facing surface 44 defined by an outer perimeter 44a and an inner perimeter 44b. Staple forming recesses 43 (e.g., a circular array or annular rows of staple forming recesses) are defined in the tissue facing surface 44 of the anvil member 42. The staple forming recesses 43 mirror staple retaining slots 51 of the staple cartridge assembly 50 (e.g., corresponding in position, size, and/or shape). The anvil assembly 40 further includes an anvil shaft 46 extending distally from the anvil member 52. The anvil shaft 46 is releasably connectable to the elongated tubular body 30 of the surgical stapling apparatus 10.

The anvil shaft 46 of the anvil assembly 40 may be connected to a rod 34 extending through the elongated tubular body 30. The rod 34 can be operably coupled to the advancing member 24 of the handle assembly 20 such that, when the anvil shaft 46 is attached to the rod 34, rotation of the advancing member 24 results in longitudinal movement of the rod 34 which, in turn, results in longitudinal movement of the anvil assembly 40 relative to the elongated tubular body 30. For example, when the advancing member 24 is rotated in a first direction, the anvil assembly 40 is moved away from the elongated tubular body 30, allowing tissue to be placed between the anvil and staple cartridge assemblies 40, 50 and, when the advancing member 24 is rotated in a second direction, the anvil assembly 40 is moved toward the elongated tubular body 30, allowing the tissue to be clamped between the anvil and staple cartridge assemblies 40, 50. It should be understood that other mechanisms for moving the anvil assembly 40 with respect to the elongated tubular body 30 are contemplated and within the purview of those skilled in the art.

As shown in FIGS. 1A and 2, the staple cartridge assembly 50 includes a tissue facing surface 52 defined by an outer perimeter 52a and an inner perimeter 52b. Staple retaining or receiving slots 51 (e.g., a circular array or annular rows of staple retaining slots) are defined in the tissue facing surface 52 of the staple cartridge assembly 50, with a staple 54 disposed in each of the staple retaining slots 51. While the staple cartridge assembly 50 is shown including three circular rows of staple retaining slots 51, it should be understood that the staple cartridge assembly 50 may include one or more rows, or partial rows, of staple retaining slots 51 in a variety of arrangements in the tissue facing surface 52 of the staple cartridge assembly 50 (e.g., the rows and/or partial rows may be circular, oval, polygonal, etc.). It should further be understood that the shape of the staple retaining slots 51 may vary (e.g., the staple retaining slots may have a curved or angled shape) to accommodate the positioning of the staples 54 relative to each other, and/or the size of the staple retaining slots 51 may vary (e.g., one or more rows of staple retaining slots may be different in size from other row(s) of staple retaining slots) to accommodate different shaped and/or sized staples 54.

A staple pusher 56 is disposed in the staple cartridge assembly 50 and has a plurality of fingers or pushers 57 that are aligned with the staple retaining slots 51. The staple pusher 56 is movable in a distal direction to drive the staples 54 out of the staple cartridge assembly 50. A knife 58, substantially in the form of an open cup having a cylindrical shape with a rim thereof defining a knife blade 59, is disposed radially inwardly of the pushers 57. The knife 58 is mounted to a surface of the staple pusher 56 so that, in use, as the staple pusher 56 is advanced distally, the knife 58 is also advanced distally (e.g., axially outward) such that after the staples 54 are driven through tissue captured between the anvil and staple cartridge assemblies 40, 50, the portions of the tissue disposed radially inwardly of the staples 54 are cut by the knife blade 59.

The movable handle members 22 of the handle assembly 20 can be operably coupled to the staple pusher 56 by, for example, a tubular member or pair of bands (not shown) that are attached to the staple pusher 56 by, for example, linkages or the like. In this way, when the movable handle members 22 are actuated, the tubular member or bands are advanced, advancing the staple pusher 56, as described above. It should be understood that other mechanisms for firing the surgical stapling apparatus 10 are contemplated and within the purview of those skilled in the art.

For a detailed description of the structure and function of exemplary surgical stapling apparatus, reference may be made to U.S. Pat. Nos. 4,473,077; 4,576,167; 5,005,749; 5,119,983; 5,588,579; 5,915,616; and 6,053,390, the entire contents of each of which are incorporated herein by reference. It should be understood that a variety of annular surgical stapling apparatus may be utilized with the surgical buttresses of the present disclosure. For example, circular staplers, such as, for example, EEA™ and CEEA™ staplers, available through Medtronic (North Haven, Conn.) may be utilized with the surgical buttresses of the present disclosure.

As shown in FIG. 2, surgical buttresses 60 are releasably attached to the tissue facing surfaces 44, 52 of the anvil and staple cartridge assemblies 40, 50, respectively. The surgical buttresses 60 may be releasably secured to the tissue facing surfaces 44, 52 of the anvil and/or staple cartridge assemblies 40, 50 via any suitable attachment feature within the purview of those skilled in the art, such as, chemical attachment features (e.g., adhesives), mechanical attachment features (e.g., mounting structures, such as tabs, pins, or straps), and/or attachment methods (e.g., welding). For a detailed description of exemplary attachment features suitable for use with a surgical buttress of the present disclosure, reference may be made to U.S. Pat. Nos. 8,584,920; 8,967,448; and 9,237,892, the entire contents of each of which are incorporated herein by reference. In embodiments, an adhesive (not explicitly shown) is disposed between the surgical buttresses 60 and the respective tissue facing surface 44, 52 of the anvil and staple cartridge assemblies 40, 50.

The surgical stapling apparatus 10 and detachable anvil assembly 40 are used in an anastomosis procedure to effect joining of tissue sections 1, 2 (e.g., intestinal or other tubular organ sections). The anastomosis procedure is typically performed using minimally invasive surgical techniques including laparoscopic means and instrumentation. At the point in the procedure shown in FIG. 2, the anvil assembly 40 has been applied to the operative site (e.g., through a surgical incision or a body orifice) and positioned within tissue section 1, the elongated tubular body 30 of the surgical stapling apparatus 10 has been inserted (e.g., through a surgical incision or a body orifice) within tissue section 2, and the anvil shaft 46 of the anvil assembly 40 has been connected to the elongated tubular body 30. The tissue sections 1, 2 are also shown temporarily secured about their respective components by conventional means such as a purse string sutures "P".

Figure 1A:
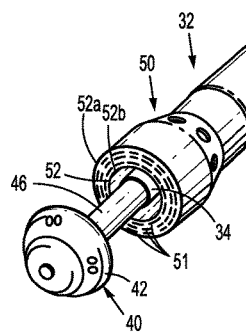

Thereafter, the anvil assembly 40 is approximated towards the elongated tubular body 30 (e.g., via advancing member 24 (FIG. 1) of the handle assembly 20) to approximate the tissue sections 1, 2. The surgical stapling apparatus 10 is then actuated (e.g., via movable handle members 22 (FIG. 1) of the handle assembly 20), firing the staples 54 from the staple cartridge assembly 50 and towards the anvil member 42 of the anvil assembly 40 to effect stapling of the tissue sections 1, 2 to one another, as well as the surgical buttresses 60 to the tissue sections 1, 2. The knife blade 59 cuts the now stapled tissue sections 1, 2, as well as any portion of the surgical buttresses 60 extending radially inwardly of the knife 58, to complete the anastomosis. Upon movement of the anvil assembly 40 away from staple cartridge assembly 50 (e.g., via advancing member 24), the surgical buttresses 60, which are now stapled to the tissue sections 1, 2, are pulled away from the anvil and staple cartridge assemblies 40, 50.

The surgical buttresses of the present disclosure are fabricated from biocompatible materials which are bioabsorbable or non-absorbable, natural or synthetic materials. It should be understood that any combination of natural, synthetic, bioabsorbable, and/or non-bioabsorbable materials may be used to form a surgical buttress. The surgical buttresses may be porous, non-porous, or combinations thereof. Suitable porous structures include, for example, fibrous structures (e.g., knitted structures, woven structures, and non-woven structures) and/or foams (e.g., open or closed cell foams). Suitable non-porous structures include, for example, films. The surgical buttresses may be a single porous or non-porous layer, or include a plurality of layers including any combination of porous and/or non-porous layers.

Porous layer(s) in a surgical buttress may enhance the ability of the surgical buttress to absorb fluid, reduce bleeding, and seal a wound. Also, the porous layer(s) may allow for tissue ingrowth to fix the surgical buttress in place. Non-porous layer(s) in a surgical buttress may enhance the ability of the surgical buttress to resist tears and perforations during the manufacturing, shipping, handling, and stapling processes. Also, non-porous layer(s) may retard or prevent tissue ingrowth from surrounding tissues thereby acting as an adhesion barrier and preventing the formation of unwanted scar tissue.

With reference now to FIG. 3A, the surgical buttress 60 has a generally circular or annular configuration defining a central aperture 61 therethrough. The central aperture 61 is sized and dimensioned to allow free passage of the anvil shaft 46 of the anvil assembly 40 therethrough. In embodiments, the central aperture 61 has a diameter that is larger than the diameter of the anvil shaft 46 of the anvil assembly 40. In some embodiments, the diameter of the central aperture 61 may be about the same as the diameter of the anvil shaft 46. The surgical buttress 60 includes discrete body segments 62 (e.g., petals) defining a discontinuous region of the surgical buttress 60, and a ring segment 64 (shown as an inner ring segment) defining a continuous region of the surgical buttress 60 that interconnects the body segments 62.

The body segments 62 are disposed in spaced relation relative to each other and extend radially outwardly from the ring segment 64. Each body segment 62 has a generally trapezoidal shape, and includes an outer edge 62a and an inner edge 62b. It should be understood that other shapes of the body segments 62 and/or the spacing therebetween are envisioned depending upon, for example, the structure of the surgical stapling apparatus 10 (e.g., the configuration of the staple retaining slots 51 of the staple cartridge assembly 50). In embodiments, the surgical buttress 60 includes eight to fourteen body segments 62 and, in some embodiments, the surgical buttress 60 includes twelve body segments 62. The body segments 62 may all be formed from the same material or may be formed from different materials. In embodiments, body segments 62 formed from a first material and body segments 62 formed from a second material may be alternately positioned around the central aperture 61 to impart different physical characteristics to the portions of the tissue to which they are stapled. The body segments 62 provide flexibility to the stapled tissue, minimizing damage thereto during manipulation of the tissue during the surgical procedure (e.g., removal of the anvil assembly 40 through the stapled tissue), as well as allowing for natural movement of the tissue to occur after completion of the surgical procedure.

The ring segment 64 is connected to the inner edges 62b of the body segments 62, and defines the central aperture 61 in an initial configuration of the surgical buttress 60. The ring segment 64 may be formed from the same material as the body segments 62, or a different material. In embodiments, the ring segment 64 is integrally formed with the body segments 62 by, for example, stamping, punching, and/or cutting the surgical buttress 60 from a buttress material. In other embodiments, the ring segment 64 is separate from the body segments 62 and attached thereto by, for example, welding, gluing, sewing, and/or heat sealing the ring segment 64 to the inner edges 62b of the body segments 62.

The body segments 62 and the ring segment 64 have a consistent construction and are configured as planar substrates or layers of buttress material. It is envisioned that the ring segment 64 may have a different construction from the body segments 62 and may be, for example, a looped filament (e.g., a stiffened suture) or a band, among other continuous annular structures for interconnecting the body segments 62 and/or reinforcing the surgical buttress 60 as should be understood by those skilled in the art.

With continued reference to FIG. 3A, in conjunction with FIGS. 1A and 1B, the surgical buttress 60 is sized and dimensioned such that the body segments 62 extend over the tissue facing surface 44, 52 of the anvil or staple cartridge assembly 40, 50, and the ring segment 64 is disposed radially inwardly of the knife 58 of the staple cartridge assembly 50. The body segments 62 may completely cover the tissue facing surface 44, 52 of the anvil or staple cartridge assembly 40, 50 to which the surgical buttress 60 is releasably secured. In embodiments, the outer edges 62a of the body segments 62 are aligned (e.g., radially) with the outer perimeter 44a, 52a of the anvil or staple cartridge assembly 40, 50, and the inner edges 62b of the body segments 62 are aligned (e.g., radially) with the inner perimeter 44b, 52b of the anvil or staple cartridge assembly 40, 50.

In some embodiments, the outer edges 62a of the body segments 62 of the surgical buttress 60 extend radially beyond the outer perimeter 44a, 52a of the anvil or staple cartridge assembly 40, 50, and/or the inner edges 62a of the body segments 62 extend radially inwardly of the inner perimeter 44b, 52b of the anvil or staple cartridge assembly 40, 50.

The entirety of the ring segment 64 is disposed radially inwardly of the knife 58 of the staple cartridge assembly 50 such that upon actuation of the surgical stapling device 10, the ring segment 64 is cut away from the surgical buttress 60, as shown in FIG. 3B. As shown in FIG. 3B, in a final configuration of the surgical buttress 60, the central aperture 61' is enlarged and the body segments 62 are connected to each other via staples 54 which form annular rows or staple lines "S1", "S2", and "S3".

In embodiments, an outer perimeter 64a of the ring segment 64 is radially aligned (and concentric) with the knife 58 of the staple cartridge assembly 50 such that upon actuation of the surgical stapling apparatus 10, only the ring segment 64 is cut away from the surgical buttress 60. In some embodiments, perforations 65 are disposed between the inner edges 62b of the body segments 62 and the outer edge 64a of the ring segment 64, and in alignment with the knife 58, to aid in the separation of the ring segment 64 from the body segments 62 during actuation of the surgical stapling apparatus 10 and/or to reduce the firing force required to cut through the stapled tissue and the surgical buttresses 60. In other embodiments, the outer perimeter 64a of the ring segment 64 is disposed radially inwardly of the knife 58 of the staple cartridge assembly 50 such that actuation of the surgical stapling apparatus 10 results in the removal of the ring segment 64 as well as portions of the body segments 62 also disposed radially inwardly of the knife 58.

Figure 4:
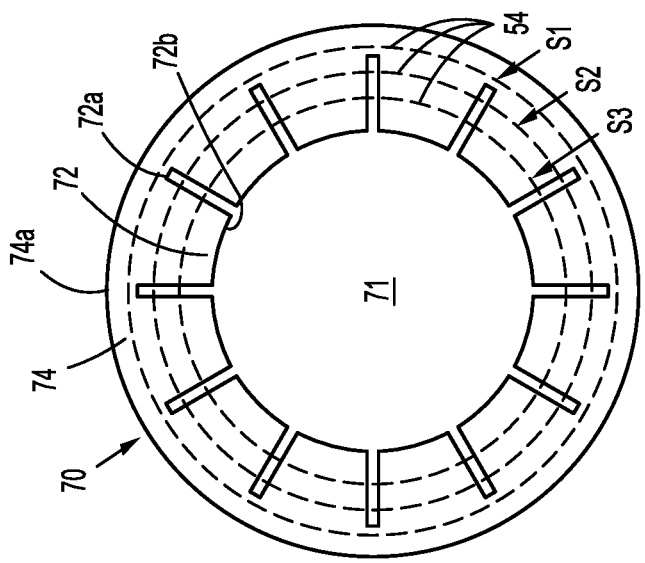
FIG. 4 is a top, plan view of a surgical buttress in accordance with another embodiment of the present disclosure.

With reference now to FIG. 4, a surgical buttress 70 in accordance with another embodiment of the present disclosure is shown. The surgical buttress 70 includes body segments 72 (e.g., petals) interconnected by a ring segment 74 (shown as an outer ring segment). The body segments 72 are substantially similar to the body segments 62 of surgical buttress 60. Each body segment 72 includes an outer edge 72a and an inner edge 72b, wherein the inner edges 72b of the body segments 72 define a central aperture 71 of the surgical buttress 70.

The ring segment 74 is connected to, and extends radially outwardly from, the outer edges 72a of the body segments 72. Similar to the ring segment 64 of the surgical buttress 60, the ring segment 72 of the surgical buttress 70 may be integrally formed with or attached to the body segments 72, may be formed from the same or different materials than the body segments 72, and/or may have the same or a different construction than the body segments 72.

The surgical buttress 70 is sized and dimensioned such that the body segments 72 extend over the staple forming recesses 43 or the staple retaining slots 51 of the anvil or staple cartridge assembly 40, 50 to which the surgical buttress 70 is releasably secured. In embodiments, the entirety of the surgical buttress 70 is disposed on the tissue facing surface 44, 52 of the anvil or staple cartridge assembly 40, 50 with an outer edge 74a of the ring segment 74 radially aligned or coincident with the outer perimeter 44a, 52a of the anvil or staple cartridge assembly 40, 50, and the inner edges 72b of the body segments 72 radially aligned with the inner perimeter 44b, 52b of the anvil or staple cartridge assembly 40, 50 such that the inner edges 72b are disposed radially inwardly of the innermost annular row "S3" of staples 54 and radially outwardly of the knife 58. Upon actuation of the surgical stapling apparatus 10, the surgical buttress 70 remains intact such that, for example, the size of the central aperture 71 does not change between initial and final configurations of the surgical buttress 70, and the body segments 72 are further connected via the annular rows "S1", "S2", and "S3" of staples 54.

As shown in FIG. 4, the ring segment 74 of the surgical buttress 70 is aligned with and configured to receive the outermost annular row "S1" of staples 54, however, other sizes and positions of the ring segment 74 relative to the staples 54 are envisioned. For example, the ring segment 74 of the surgical buttress 70 may be positioned radially outwardly of the staple forming recesses 43 or staple forming slots 51 of the anvil or staple cartridge assembly 40, 50, or the ring segment 74 may be sized and positioned to receive the outermost and middle annular rows "S1", "S2" of staples 54.

In some embodiments, the outer edge 74a of the ring segment 74 of the surgical buttress 70 may extend beyond the outer perimeter 44a, 52a of the anvil or staple cartridge assembly 40, 50, and/or the inner edges 72a of the body segments 72 may extend radially inwardly of the inner perimeter 44b, 52b of the anvil or staple cartridge assembly 40, 50. In certain embodiments, the ring segment 74 is disposed radially outwardly of the anvil or staple cartridge assembly 40, 50 and/or the inner edges 72a of the body segments 72 extend radially inwardly of the knife 58 of the staple cartridge assembly 50.

Figure 5:
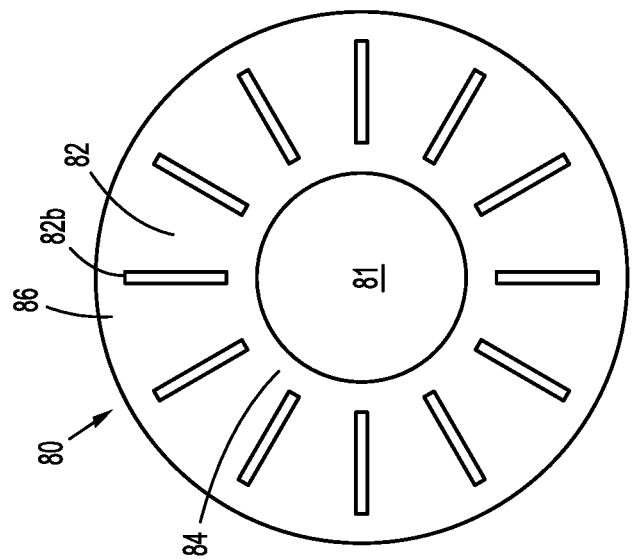
FIG. 5 is a top, plan view of a surgical buttress in accordance with yet another embodiment of the present disclosure.

As shown in FIG. 5, a surgical buttress 80 of the present disclosure may include body segments 82 and more than one ring segment 84, 86 interconnecting the body segments 82. The first ring segment 84 is disposed radially inwardly of the knife 58 of the staple cartridge assembly 50 as described, for example, with respect to the ring segment 64 of the surgical buttress 60, and the second ring segment 86 is disposed radially outwardly of the knife 58. The second ring segment 86 may extend radially beyond outer edges 82a of the body segments 82 as described, for example, with respect to the ring segment 74 of the surgical buttress 70.

A ring segment of a surgical buttress of the present disclosure, when disposed radially outwardly of the knife of the staple cartridge assembly, may aid in preventing strictures and/or stenosis of the stapled tissue. For example, as shown in FIG. 4, the ring segment 74 of the surgical buttress 70, and/or, as shown in FIG. 5, the second ring segment 86 of the surgical buttress 80, may aid in keeping open and/or reinforcing stapled tissue sections. While the ring segment 74 and the second ring segment 86 of FIGS. 4 and 5, respectively, are disposed about an outer portion of the respective surgical buttresses 70, 80, it should be understood that a ring segment may be disposed about any portion of a surgical buttress disposed radially outwardly of, and in spaced relation to, the knife 58 of the staple cartridge assembly 50.

Figure 6:
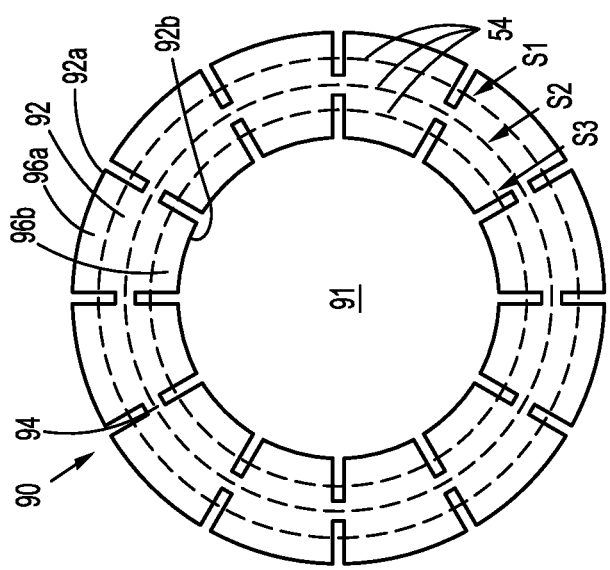
FIG. 6 is a top, plan view of a surgical buttress in accordance with another embodiment of the present disclosure.

As shown in FIG. 6, a surgical buttress 90 includes body segments 92 defining a central aperture 91 therethrough, and a ring segment 94 (shown as a central ring segment) interconnecting the body segments 92. The continuous ring segment 94 bifurcates or otherwise divides each body segment 92, and defines outer and inner sections 96a, 96b of body segments 92. In the illustrated embodiment, the ring segment 94 bifurcates the body segments 92 about a central portion thereof (e.g., midway between outer and inner edges 92a, 92b of the body segments 92), however, it is envisioned that the ring segment 94 may be otherwise positioned between the outer and inner edges 92a, 92b of the body segments 92.

As shown in FIG. 6, the ring segment 94 of the surgical buttress 90 is aligned with and configured to receive the middle annular row "S2" of staples 54, however, as discussed above, other sizes and positions of the ring segment 94 are envisioned. Further, the inclusion of additional ring segments are also envisioned (e.g., more than one ring segment disposed radially outwardly of the knife 58 of the staple cartridge assembly 50).

It should be understood that while the surgical stapling apparatus 10 is shown including surgical buttresses 60 disposed on both the anvil and the staple cartridge assemblies 40, 50, the surgical stapling apparatus 10 may include only one surgical buttress 60 disposed on either the anvil assembly 40 or the staple cartridge assembly 50. It should be further understood that any of the surgical buttresses 60, 70, 80, 90 may be disposed on the anvil and/or staple cartridge assemblies 40, 50 depending on, for example, the surgical application and/or desired placement of the buttress material relative to tissue as should be understood by those skilled in the art. It is envisioned that the surgical buttress 60, 70, 80, 90 may be, additionally or alternatively, positioned on the anvil shaft 46 of the anvil assembly 40 following the connection of the anvil assembly 40 to the tissue section 1 such that the surgical buttress 60, 70, 80, 90 is stapled between the tissue sections 1, 2 following actuation of the surgical stapling apparatus 10.

The surgical buttress(es) 60, 70, 80, 90 may be pre-loaded (e.g., by the manufacturer) onto the anvil assembly 40 and/or the staple cartridge assembly 50. Additional or replacement surgical buttresses 60, 70, 80, 90 may be secured to the respective anvil and/or staple cartridge assemblies 40, 50, as needed or desired.

The surgical buttresses described herein may also be configured for use with other surgical apparatus, such as electromechanical surgical devices as described, for example, in U.S. Patent Appl. Pub. Nos. 2015/0157320 and 2015/0157321, the entire contents of each of which are incorporated herein by reference.

Persons skilled in the art will understand that the devices and methods specifically described herein and illustrated in the accompanying figures are non-limiting exemplary embodiments, and that the description, disclosure, and figures should be construed merely exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another exemplary embodiment without departing from the scope of the present disclosure, and that such modifications and variations are also intended to be included within the scope of the present disclosure. Accordingly, the subject matter of the present disclosure is not to be limited by what has been particularly shown and described.

What is claimed is:

1. A surgical stapling apparatus comprising:
a staple cartridge assembly including a tissue facing surface defined by a radial outer perimeter and a radial inner perimeter;
an anvil assembly operatively associated with the staple cartridge assembly, the anvil assembly including a tissue facing surface defined by a radial outer perimeter and a radial inner perimeter; and
a surgical buttress having an annular configuration defining a central aperture therethrough and including discrete body segments disposed in radial spaced relation relative to each other and a ring segment interconnecting the body segments, the body segments defining a discontinuous region of the surgical buttress and the ring segment defining a continuous region of the surgical buttress, the discontinuous region extending to at least one of a radial inner terminal edge or a radial outer terminal edge of the surgical buttress, the body segments releasably attached to the tissue facing surface of the staple cartridge assembly or the anvil assembly, each of the body segments including an outer edge and an inner edge, the outer and inner edges aligned with the respective radial outer and inner perimeters of the tissue facing surface of the staple cartridge assembly or the anvil assembly.

2. The surgical stapling apparatus according to claim 1, wherein the ring segment of the surgical buttress extends radially inwardly from the inner edges of the body segments.

3. The surgical stapling apparatus according to claim 2, wherein a radial inner edge of the ring segment defines the radial inner terminal edge of the surgical buttress.

4. The surgical stapling apparatus according to claim 2, wherein the staple cartridge assembly includes an annular knife disposed radially inwardly of the tissue facing surface, and the ring segment of the surgical buttress is positioned radially inwardly of the annular knife.

5. The surgical stapling apparatus according to claim 4, wherein a radial outer edge of the ring segment is aligned with the annular knife of the staple cartridge assembly such that actuation of the annular knife severs the ring segment from the body segments.

6. The surgical stapling apparatus according to claim 4, wherein the surgical buttress includes perforations disposed in an annular configuration between the body segments and the ring segment, the perforations aligned over the annular knife of the staple cartridge assembly.

7. The surgical stapling apparatus according to claim 2, wherein the outer edges of the body segments define the radial outer terminal edge of the surgical buttress.

8. The surgical stapling apparatus according to claim 1, wherein the ring segment of the surgical buttress extends radially outwardly from the outer edges of the body segments.

9. The surgical stapling apparatus according to claim 8, wherein a radial outer edge of the ring segment of the surgical buttress defines the radial outer terminal edge of the surgical buttress.

10. The surgical stapling apparatus according to claim 8, wherein the inner edges of the body segments of the surgical buttress define the radial inner terminal edge of the surgical buttress.

11. The surgical stapling apparatus according to claim 1, wherein the ring segment of the surgical buttress bifurcates each of the body segments, and the inner and outer edges of the body segments define the respective radial inner and outer terminal edges of the surgical buttress.

12. The surgical stapling apparatus according to claim 11, wherein the tissue facing surface of the staple cartridge assembly has staple retaining slots defined therein and the tissue facing surface of the anvil assembly has staple forming recesses defined therein, and the ring segment of surgical buttress is disposed over at least one of the annular row of the staple retaining slots or the staple forming recesses of the staple cartridge assembly or the anvil assembly to which the surgical buttress is releasably attached.

13. The surgical stapling apparatus according to claim 1, wherein the anvil assembly includes an anvil member including the tissue facing surface and an anvil shaft extending from the anvil member, and the central aperture of the surgical buttress has a diameter larger than a diameter of the anvil shaft such that the surgical buttress is disposed radially outwardly in spaced relation relative to the anvil shaft.

14. The surgical stapling apparatus according to claim 1, wherein an adhesive is disposed between the surgical buttress and the tissue facing surface of the staple cartridge assembly or the anvil assembly to releasably retain the surgical buttress thereon.

15. The surgical stapling apparatus according to claim 1, wherein each of the body segments of the surgical buttress has a generally trapezoidal shape.

16. The surgical stapling apparatus according to claim 1, wherein the discontinuous region extends to one of the radial inner or outer terminal edges of the surgical buttress and the continuous region extends to the other of the radial inner or outer terminal edges of the surgical buttress.

17. The surgical stapling apparatus according to claim 1, wherein the discontinuous region extends to both of the radial inner and outer terminal edges of the surgical buttress, and the continuous region extends through a central portion of the surgical buttress.

18. A staple cartridge assembly for use with a surgical stapling apparatus, the staple cartridge assembly comprising:
a staple cartridge including a tissue facing surface defined by a radial outer perimeter and a radial inner perimeter; and
a surgical buttress having an annular configuration defining a central aperture therethrough and including discrete body segments disposed in radial spaced relation relative to each other and a ring segment interconnecting the body segments, the body segments defining a discontinuous region of the surgical buttress and the ring segment defining a continuous region of the surgical buttress, the discontinuous region extending to at least one of a radial inner terminal edge or a radial outer terminal edge of the surgical buttress, the body segments releasably attached to the tissue facing surface of the staple cartridge, each of the body segments including an outer edge and an inner edge, the outer and inner edges aligned with the respective radial outer and inner perimeters of the tissue facing surface of the staple cartridge.

19. An anvil assembly for use with a surgical stapling apparatus, the anvil assembly comprising:

an anvil member including a tissue facing surface defined by a radial outer perimeter and a radial inner perimeter; and a surgical buttress having an annular configuration defining a central aperture therethrough and including discrete body segments disposed in radial spaced relation relative to each other and a ring segment interconnecting the body segments, the body segments defining a discontinuous region of the surgical buttress and the ring segment defining a continuous region of the surgical buttress, the discontinuous region extending to at least one of a radial inner terminal edge or a radial outer terminal edge of the surgical buttress, the body segments releasably attached to the tissue facing surface of the anvil member, each of the body segments including an outer edge and an inner edge, the outer and inner edges aligned with the respective radial outer and inner perimeters of the tissue facing surface of the anvil member.

20. A surgical stapling apparatus comprising:

a staple cartridge assembly including a tissue facing surface defined by a radial outer perimeter and a radial inner perimeter, the staple cartridge assembly including an annular knife disposed radially inwardly of the tissue facing surface;

an anvil assembly operatively associated with the staple cartridge assembly, the anvil assembly including a tissue facing surface defined by a radial outer perimeter and a radial inner perimeter; and a surgical buttress having an annular configuration defining a central aperture therethrough, the surgical buttress including discrete body segments disposed in radial spaced relation relative to each other, a ring segment interconnecting the body segments, and perforations disposed in an annular configuration between the body segments and the ring segment, the body segments releasably attached to the tissue facing surface of the staple cartridge assembly or the anvil assembly, each of the body segments including an outer edge and an inner edge, the outer and inner edges aligned with the respective radial outer and inner perimeters of the tissue facing surface of the staple cartridge assembly or the anvil assembly, the ring segment of the surgical buttress positioned radially inwardly of the annular knife and the perforations aligned over the annular knife.

\* \* \* \* \*